United States Patent [19]

Brown

[11] Patent Number: 4,631,186

[45] Date of Patent: Dec. 23, 1986

[54] METHOD OF TREATING FINGERNAILS AND CUTICLES

[76] Inventor: Ann H. Brown, 4848 Dexter St., N.W., Washington, D.C. 20007

[21] Appl. No.: 352,098

[22] Filed: Feb. 25, 1982

Related U.S. Application Data

[63] Continuation of Ser. No. 143,150, Apr. 23, 1980, abandoned.

[51] Int. Cl.$^4$ .................... A61K 7/135; A61K 7/021; A61K 7/04
[52] U.S. Cl. ........................................ 424/61; 424/62; 424/63
[58] Field of Search .................. 424/61, 62, 63, 364

[56] References Cited

U.S. PATENT DOCUMENTS

| | | | |
|---|---|---|---|
| 3,235,457 | 2/1966 | Laden | 424/274 |
| 3,510,554 | 5/1970 | Balsiger | 424/61 |
| 3,887,702 | 6/1975 | Baldwin | 424/61 |

FOREIGN PATENT DOCUMENTS 1439834  5/1966  France .
1337461  11/1973  United Kingdom .

OTHER PUBLICATIONS

USDA, Comp. of Foods, Agriculture Handbook No. 8, pp. 22, 184.
Enikeev, Chem. Abs., vol. 54, 1960, p. 9011a.
Korablev, Chem. Abs., vol. 50, 1956, p. 3707e.
Mahdi, Chem. Abs., vol. 54, 1960, p. 2626h.
Tanner, Chem. Abs., vol. 70, 1967, Ab. No. 46279w.
Vigorov, Chem. Abs., vol. 73, 1970, Ab. No. 2737w.

*Primary Examiner*—Albert T. Meyers
*Assistant Examiner*—F. L. Abramson
*Attorney, Agent, or Firm*—Cushman, Darby & Cushman

[57] ABSTRACT

Nails, particularly fingernails, are strengthened and their growth is enhanced by treating them with sour cherry juice. Also the cuticles benefit by this treatment.

10 Claims, No Drawings

METHOD OF TREATING FINGERNAILS AND CUTICLES

This is a continuation of application Ser. No. 143,150 filed Apr. 23, 1980, now abandoned.

BACKGROUND OF THE INVENTION

This invention relates to a method of treating nails and cuticles, particularly human fingernails and toenails.

It is an object of the present invention to strengthen such nails, and also to improve the cuticles, while making them more resilient without brittleness.

A further object is to help the growth of such nails and to improve their appearance.

It has now been found that these objects can be attained and the quality of nails, more especially human fingernails and toenails, can be enhanced and splitting, cracking and the like, of both the nails and cuticles can be reduced and growth of the nails and cuticles stimulated by topically treating the nails with sour cherry juice.

The analysis of sour cherries is set forth in "Composition of Foods", Agriculture Handbook No. 8 of the U.S. States Department of Agriculture, October 1975 reprinting of page 22.

While there can be used the juice of any sour cherries, at present Montmorency cherry is preferred.

There can be used the natural cherry juice. To preserve the juice, however, so that it can be stored for long periods of time, it is preferred to sterilize the cherry juice. This can be done in any conventional manner, e.g. by heating the cherry juice to 90° C., filling it into hot sterilized jars, capping the jars immediately, turning them upside down, e.g. for 3-4 minutes (to sterilize the caps) and then cooling the jars as quickly as possible to prevent changes in the composition of the cherry juice.

Instead of sterilization, less preferably the cherry juice can be preserved by addition of 0.1% of sodium or potassium benzoate.

While the sour cherry juice can be used to strengthen either fingernails or toenails, at present it is preferred to treat fingernails and their cuticles.

The sour cherry juice can be applied topically to the nails in very simple manner. Thus, in an illustrative form of the invention, it has been found that the nails and cuticles, e.g. fingernails, can be treated by simply being dipped or immersed in the sour cherry juice every night at bedtime for two weeks and then 2-3 times a week thereafter. After removing the nails from the solution the nails dry very quickly.

Alternatively the sour cherry juice can be applied by brushing the sour cherry juice on the nails and cuticles.

For best results during at least the initial two week period no other preparation, e.g. nail polish or lacquer, should be applied to the nails.

What is claimed is:

1. A method for improving the quality and strength of nails and their cuticles consisting essentially of applying topically to the nails and cuticles an effective amount of a composition consisting essentially of sour cherry juice.

2. The method of claim 1 wherein the nails are fingernails.

3. The method of claim 2 wherein the juice is Montmorency sour cherry juice.

4. The method of claim 3 wherein the sour cherry juice is sterilized sour cherry juice.

5. The method of claim 2 wherein the cherry juice is sterilized sour cherry juice.

6. The method of claim 2 wherein the cherry juice is unstabilized natural sour cherry juice.

7. The method of claim 2 wherein the sour cherry juice is applied to a fingernail and cuticle by immersing the fingernail and cuticle in the sour cherry juice.

8. The method of claim 1 wherein the composition consists of sour cherry juice.

9. The method of claim 1 wherein the sour cherry juice is applied for a period of at least two weeks.

10. The method of claim 7 wherein the sour cherry juice is applied for a period of at least two weeks.

* * * * *